United States Patent
Cutting et al.

(10) Patent No.: US 8,448,457 B2
(45) Date of Patent: May 28, 2013

(54) SYSTEMS AND METHODS FOR USE IN FREEZING, THAWING, AND STORING BIOPHARMACEUTICAL MATERIALS

(75) Inventors: Jonathan Cutting, Fairfield, CA (US); Isabelle Gay, Peypin (FR); Oscar Werner Reif, Hannover (DE)

(73) Assignee: Sartorius Stedim North America Inc., Bohemia, NY (US)

( * ) Notice: Subject to any disclaimer, the term of this patent is extended or adjusted under 35 U.S.C. 154(b) by 786 days.

(21) Appl. No.: 12/624,031

(22) Filed: Nov. 23, 2009

(65) Prior Publication Data

US 2011/0120151 A1    May 26, 2011

(51) Int. Cl.
*F25C 1/00* (2006.01)
(52) U.S. Cl.
USPC ............................................. 62/66; 62/530
(58) Field of Classification Search
USPC ................... 62/66, 441, 457.2, 530; 165/64
See application file for complete search history.

(56) References Cited

U.S. PATENT DOCUMENTS

| | | | | |
|---|---|---|---|---|
| 3,940,249 A | * | 2/1976 | McClurg | 436/174 |
| 3,942,668 A | | 3/1976 | Eberle et al. | |
| 4,011,736 A | | 3/1977 | Harrison | |
| 4,292,817 A | * | 10/1981 | Loucks | 62/457.5 |
| 4,377,077 A | * | 3/1983 | Granlund | 62/457.1 |
| 4,498,312 A | * | 2/1985 | Schlosser | 62/457.2 |
| 4,502,295 A | * | 3/1985 | Toledo-Pereyra | 62/463 |
| 5,103,651 A | | 4/1992 | Coelho et al. | |
| 5,215,208 A | * | 6/1993 | Jackson | 220/516 |
| 5,405,012 A | * | 4/1995 | Shindler et al. | 206/569 |
| 5,417,082 A | * | 5/1995 | Foster et al. | 62/457.1 |
| 5,435,142 A | * | 7/1995 | Silber | 62/60 |
| 5,548,967 A | | 8/1996 | Ghiraldi | |
| 5,638,686 A | | 6/1997 | Coelho et al. | |
| 6,079,404 A | * | 6/2000 | Salyer | 126/263.03 |
| 6,196,296 B1 | | 3/2001 | Wisniewski et al. | |
| 6,220,051 B1 | | 4/2001 | Takasugi | |
| 6,302,327 B1 | | 10/2001 | Coelho et al. | |

(Continued)

FOREIGN PATENT DOCUMENTS

| | | |
|---|---|---|
| GB | 2236694 A | 4/1991 |
| WO | WO 97/29331 | 8/1997 |
| WO | WO 98/34078 | 8/1998 |
| WO | WO 01/02268 A1 | 1/2001 |

OTHER PUBLICATIONS

Notification of Transmittal of the International Search Report and Written Opinion, mailed Jun. 9, 2011, from corresponding International Application No. PCT/US2010/057752.

(Continued)

*Primary Examiner* — Mohammad Ali
(74) *Attorney, Agent, or Firm* — Heslin Rothenberg Farley & Mesiti P.C.; Victor A. Cardona, Esq.

(57) ABSTRACT

A system for use in freezing, thawing, transporting or storing biopharmaceutical materials which includes a container, a holder and plurality of heat transfer members. The container is configured to hold biopharmaceutical materials therein. The holder has a cavity for receiving the container and includes an interior surface bounding the cavity. A plurality of pockets contact outer surfaces of the container and is received in the cavity. Each pocket of the plurality of pockets includes a pocket cavity. A heat transfer member actively controls the temperature of biopharmaceutical materials held in the container and is received in the pocket cavity.

18 Claims, 12 Drawing Sheets

Ready    Insertion    Freeze/Thaw    Removal    Ready

U.S. PATENT DOCUMENTS

| | | | |
|---|---|---|---|
| 6,307,871 B1 * | 10/2001 | Heberle | 372/34 |
| 6,361,746 B1 * | 3/2002 | Wlodarski | 422/561 |
| 6,453,683 B1 | 9/2002 | Wisniewski et al. | |
| 6,609,392 B1 * | 8/2003 | Brown | 62/457.1 |
| 6,635,414 B2 | 10/2003 | Wisniewski | |
| 6,775,473 B2 | 8/2004 | Augustine et al. | |
| 6,786,054 B2 | 9/2004 | Voute et al. | |
| 6,945,056 B2 | 9/2005 | Brown et al. | |
| 6,996,995 B2 | 2/2006 | Voute et al. | |
| 7,055,583 B2 | 6/2006 | Filippi et al. | |
| 7,104,074 B2 | 9/2006 | Voute et al. | |
| 7,137,261 B2 | 11/2006 | Brown et al. | |
| 7,263,855 B2 | 9/2007 | Meyer et al. | |
| 7,337,908 B2 | 3/2008 | Dedmon | |
| 7,353,658 B2 | 4/2008 | Voute et al. | |
| 2004/0226309 A1 | 11/2004 | Broussard | |
| 2007/0062670 A1 | 3/2007 | Radelet et al. | |
| 2008/0000624 A1 | 1/2008 | Symonds et al. | |

OTHER PUBLICATIONS

Partial International Search Report from corresponding International Application No. PCT/US2010/057752, dated Mar. 24, 2011.

* cited by examiner

SYSTEMS AND METHODS FOR USE IN FREEZING, THAWING, AND STORING BIOPHARMACEUTICAL MATERIALS

TECHNICAL FIELD

This invention relates, in general, to biopharmaceutical materials, preservation methods and systems, and more particularly to systems and methods for freezing, storing, transporting, and thawing biopharmaceutical materials.

BACKGROUND ART

Preservation of biopharmaceutical materials is important in the manufacture, use, transport, storage and sale of such materials. For example, biopharmaceutical materials are often preserved by freezing between processing steps and during storage. Similarly, biopharmaceutical materials are often frozen and thawed as part of the development process to enhance the quality or to simplify the development process. Biopharmaceutical materials may also need to be stored and shipped at a certain temperature range.

When freezing biopharmaceutical materials, the overall quality, and in particular pharmaceutical activity, of the biopharmaceutical materials is desirably preserved, without substantial degradation of the biopharmaceutical materials.

The preservation of biopharmaceutical material, particularly in bulk quantities, often involves placing a container containing liquid biopharmaceutical material in a cabinet freezer, chest freezer or walk-in freezer and allowing the biopharmaceutical material to freeze. Specifically, the container, which is typically one or more liters in volume and may range up to ten or more liters, is often placed on a shelf in the cabinet freezer, chest freezer or walk-in freezer and the biopharmaceutical material is allowed to freeze. These containers may be stainless-steel vessels, plastic bottles or carboys, or plastic bags. They are typically filled with a specified volume to allow for freezing and expansion and then transferred into the freezers at temperatures typically ranging from negative 20 degrees Celsius to negative 70 degrees Celsius or below.

Single-use bulk storage containers such as plastic bags or other flexible containers often are damaged, leading to loss of the biopharmaceutical material. Particularly, the volumetric expansion of the biopharmaceutical materials during freezing could generate excessive pressure in an over filled bag or in a pocket of occluded liquid adjoining the bag material, possibly leading to rupture or damage to the integrity of the bag. Moreover, handling of such disposable containers, such as plastic bags, during freezing, thawing, or transportation of these containers often results in damage thereof, due, for example, to shock, abrasion, impact, or other mishandling events arising from operator errors or inadequate protection of the bags in use.

Similarly, thawing of bulk biopharmaceutical materials may involve removing them from a freezer and allowing them to thaw at room temperature. In certain situations thawing can also lead to product loss. In addition, in certain situations rapid thawing of biopharmaceutical materials may result in less product loss than slower thawing. Further, it may also be desirable to control temperature of the biopharmaceutical materials during a thawing process since exposure of some biopharmaceutical materials to elevated temperatures in certain situations may also lead to product loss. For example, it may be desirable to maintain a thawing biopharmaceutical material at about 0° C. when still in liquid and solid form during thawing thereof. In situations where thawing is desirable it is necessary to protect the biopharmaceutical material from damage which may occur due to impact or rupture to the containers.

In another example, jacketed stainless steel vessels receive biopharmaceutical materials therein for freezing and thawing. In a further example, bags are received in plate freezers to control the temperature of biopharmaceutical materials in such bags. However, jacket stainless steel vessels require significant capital costs and present a risk of cross-contamination. Further, the use of plate freezers to control the temperature of biopharmaceutical materials in bags or flexible containers requires a significant investment in the cost of the plate freezers themselves. Further, the flexible containers used with such plate freezers lack robustness, and may thus be damaged in use.

Thus, there is a need for systems and methods for freezing, thawing, and storing biopharmaceutical materials, including containers and holders for such containers usable for the freezing, thawing, transporting and storing of biopharmaceutical materials.

SUMMARY OF THE INVENTION

The present invention provides, in a first aspect, a system for use in freezing, thawing, transporting, or storing biopharmaceutical materials which includes a container, a holder and a heat transfer member. The container is configured to hold biopharmaceutical materials therein. The holder has a holder cavity for receiving the container and includes an interior surface bounding the cavity. A plurality of pockets contact an outer surface of the container means and is received in the holder cavity. Each pocket of the plurality of pockets includes a pocket cavity. The heat transfer member actively controls the temperature of biopharmaceutical materials held in the container and is received in the pocket cavity.

The present invention provides, in a second aspect, a system for use in freezing, thawing, transporting, or storing biopharmaceutical materials which includes a container means and a holder. The container means is configured to hold biopharmaceutical materials therein. A plurality of pockets contacts an outer surface of the container means. Each pocket of the plurality of pockets includes a pocket cavity. The holder has a holder cavity for receiving the container and the plurality of pockets and includes an interior surface bounding the cavity. The interior surface includes two contact surfaces contacting the plurality of pockets on opposite sides of the container.

The present invention provides, in a third aspect, a method for use in freezing, thawing, transporting, or storing biopharmaceutical materials which includes receiving a container holding biopharmaceutical materials in a holder having a holder cavity. A plurality of pockets is received in the holder cavity. The plurality of pockets contacts outer surfaces of the container means with each pocket of the plurality pockets including a pocket cavity. A heat transfer member is received in the pocket cavity. A temperature of the heat transfer member is actively controlled to control a temperature of the biopharmaceutical materials held in the container.

BRIEF DESCRIPTION OF THE DRAWINGS

The subject matter which is regarded as the invention is particularly pointed out and distinctly claimed in the claims at the conclusion of the specification. The foregoing and other features, and advantages of the invention will be readily understood from the following detailed description of preferred embodiments taken in conjunction with the accompanying drawings in which:

DETAILED DESCRIPTION

Figure 1:
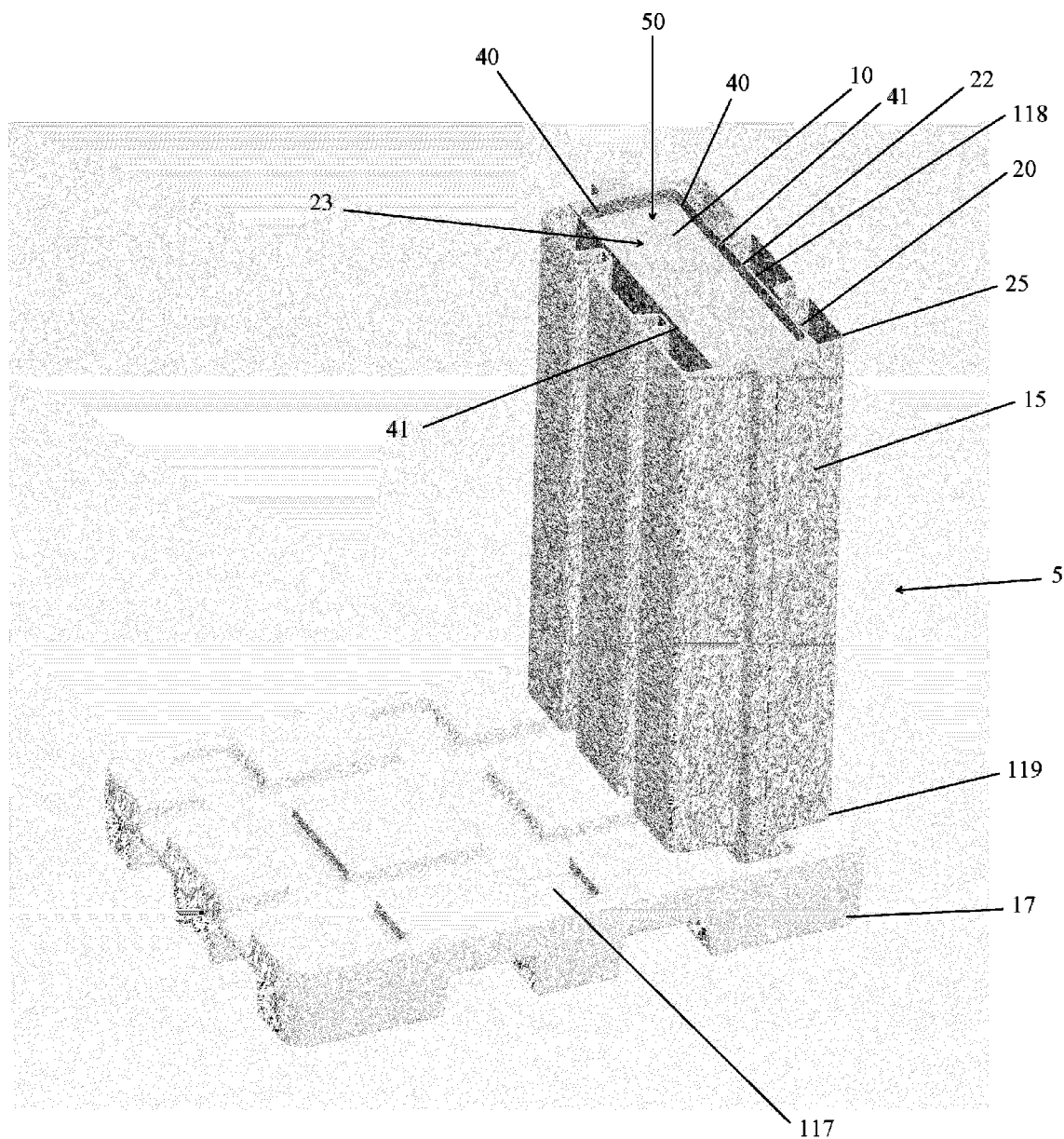
FIG. 1 is a perspective view of a holder receiving a container holding biopharmaceutical materials and the holder received on a pallet base in accordance with the present invention.

In accordance with the principles of the present invention, systems and methods for freezing, thawing and storing biopharmaceutical materials are provided.

In an exemplary embodiment depicted in FIGS. 1-4, a system 5 for cooling, freezing, preserving, processing and thawing biopharmaceutical materials is shown. The system may include a sterile container, such as a flexible container 10 in the form of a bag, configured to contain the biopharmaceutical materials and configured to be received in and supported by a supporting and/or protective structure, such as a holder 15. Holder may be received in a base 17 having a plurality of recesses or grooves 117 for receiving and supporting a bottom end 119 of holder 15.

Figure 2:
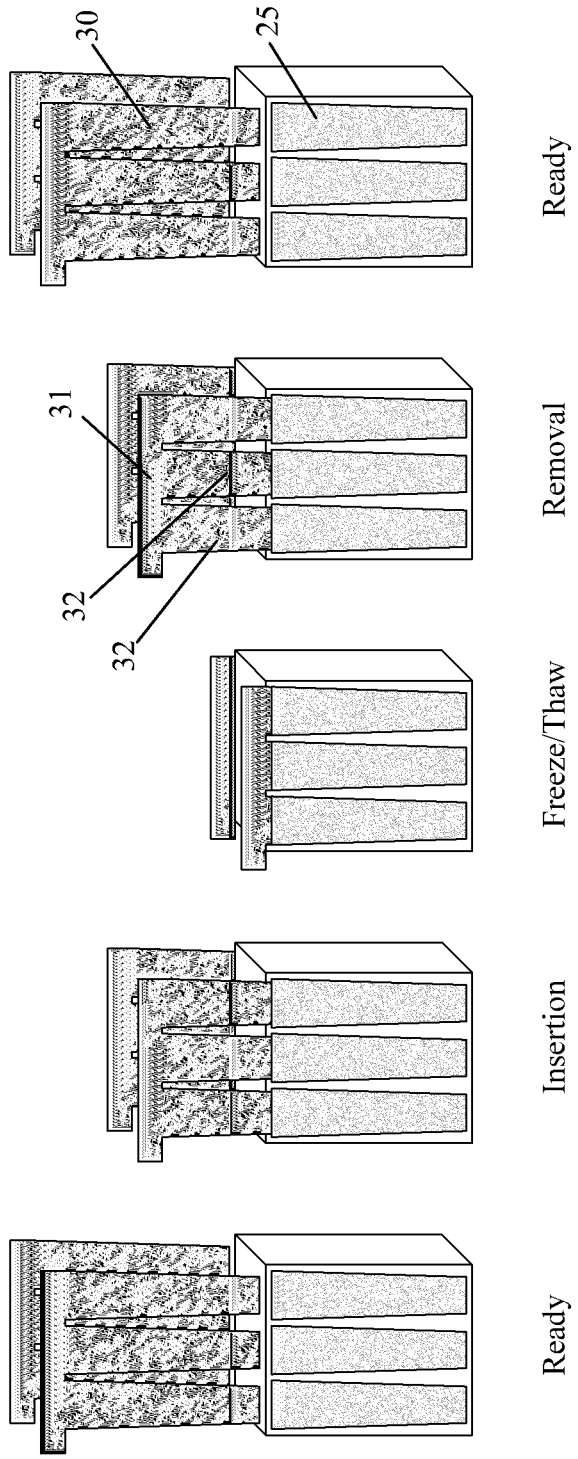
FIG. 2 is a side perspective view of a process for inserting heat transfer members into pockets of the holder of FIG. 1 and controlling the temperature of biopharmaceutical materials held in the holder.
Figure 3A:
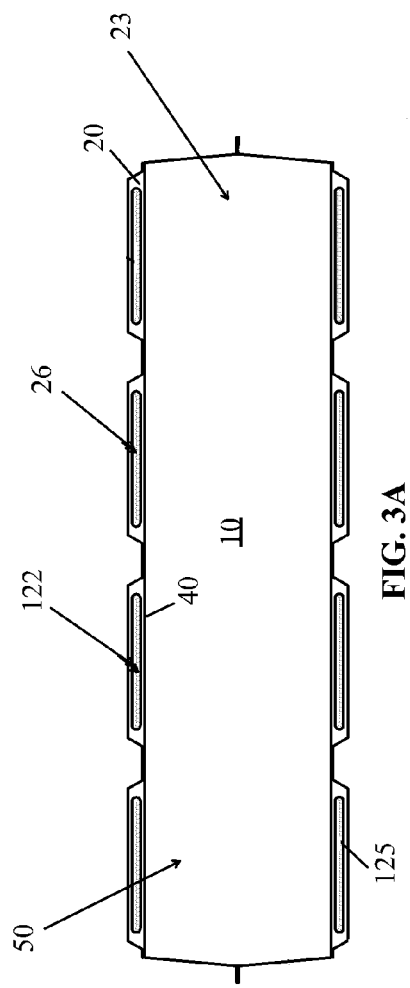
FIG. 3A is a horizontal cross section through the holder of FIG. 3.
Figure 3:
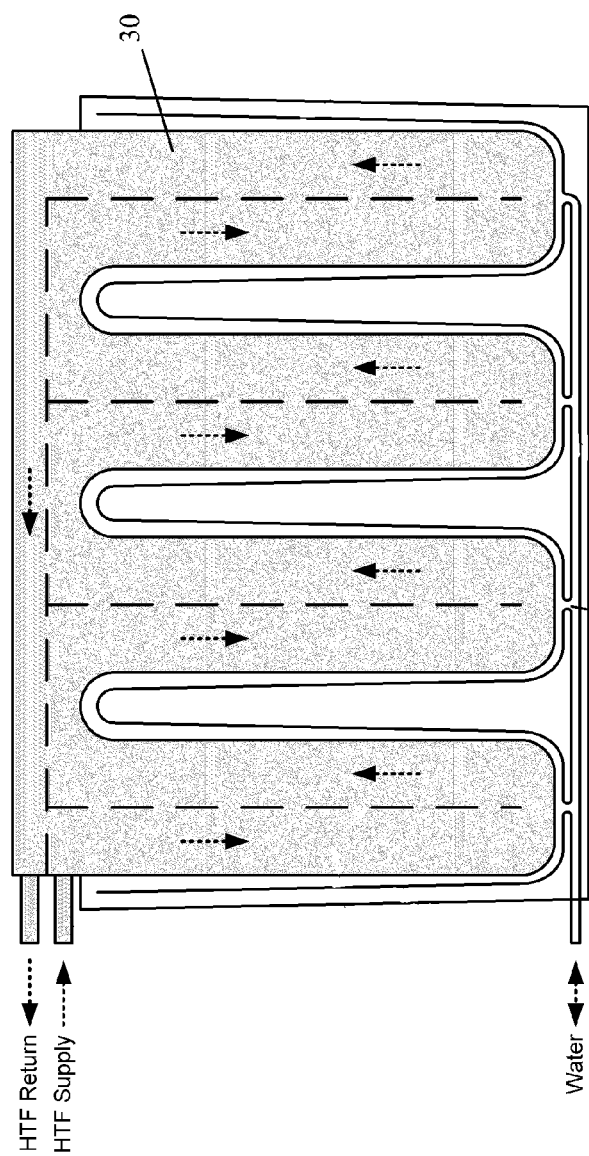
FIG. 3 is a vertical cross section through the holder of FIG. 1 illustrating flow of heat transfer fluid through heat transfer members located in pockets on a side of the holder.
Figure 4:
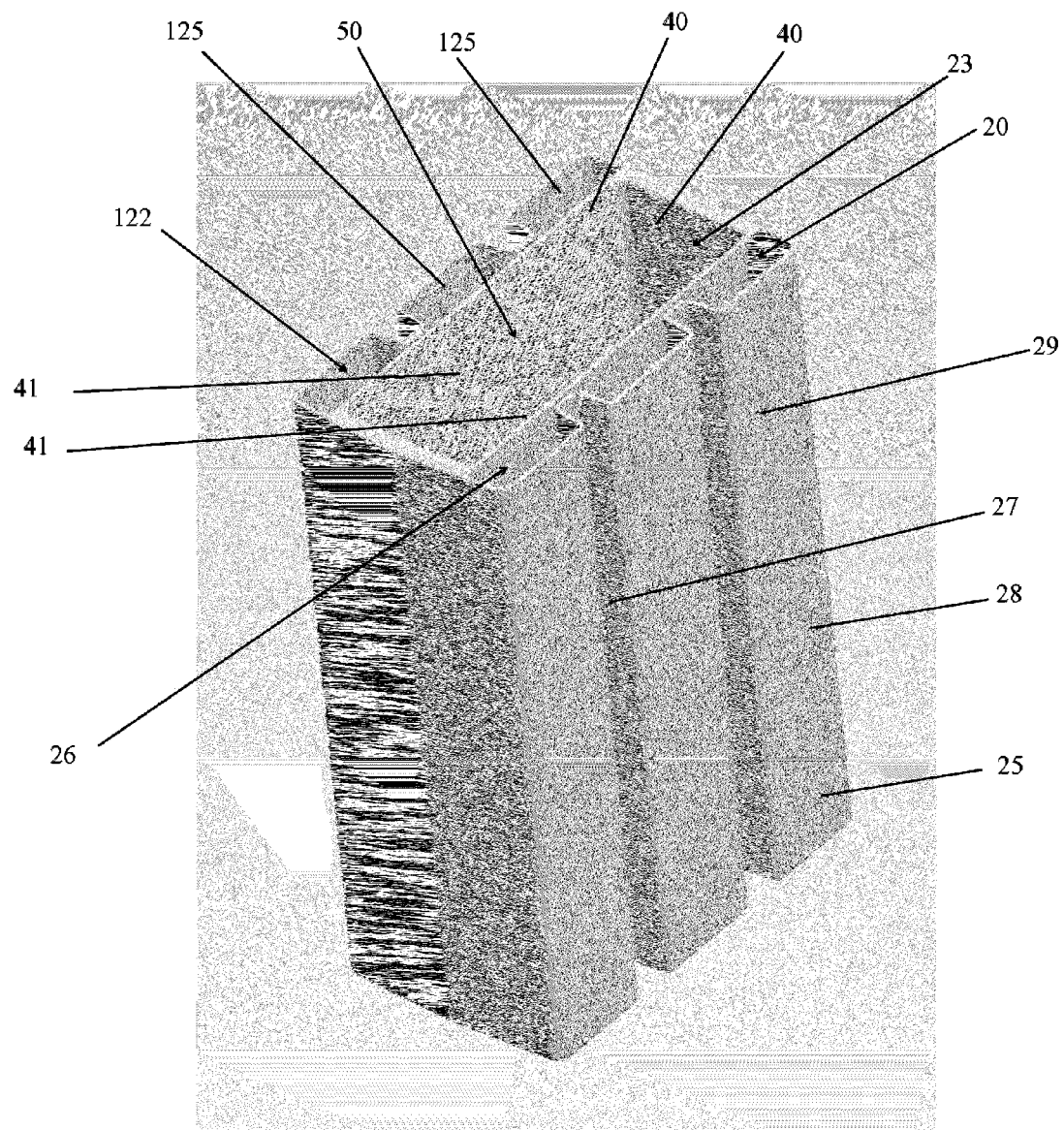
FIG. 4 is a perspective view of the holder of FIG. 1 without the container in the cavity thereof.
Figure 7:
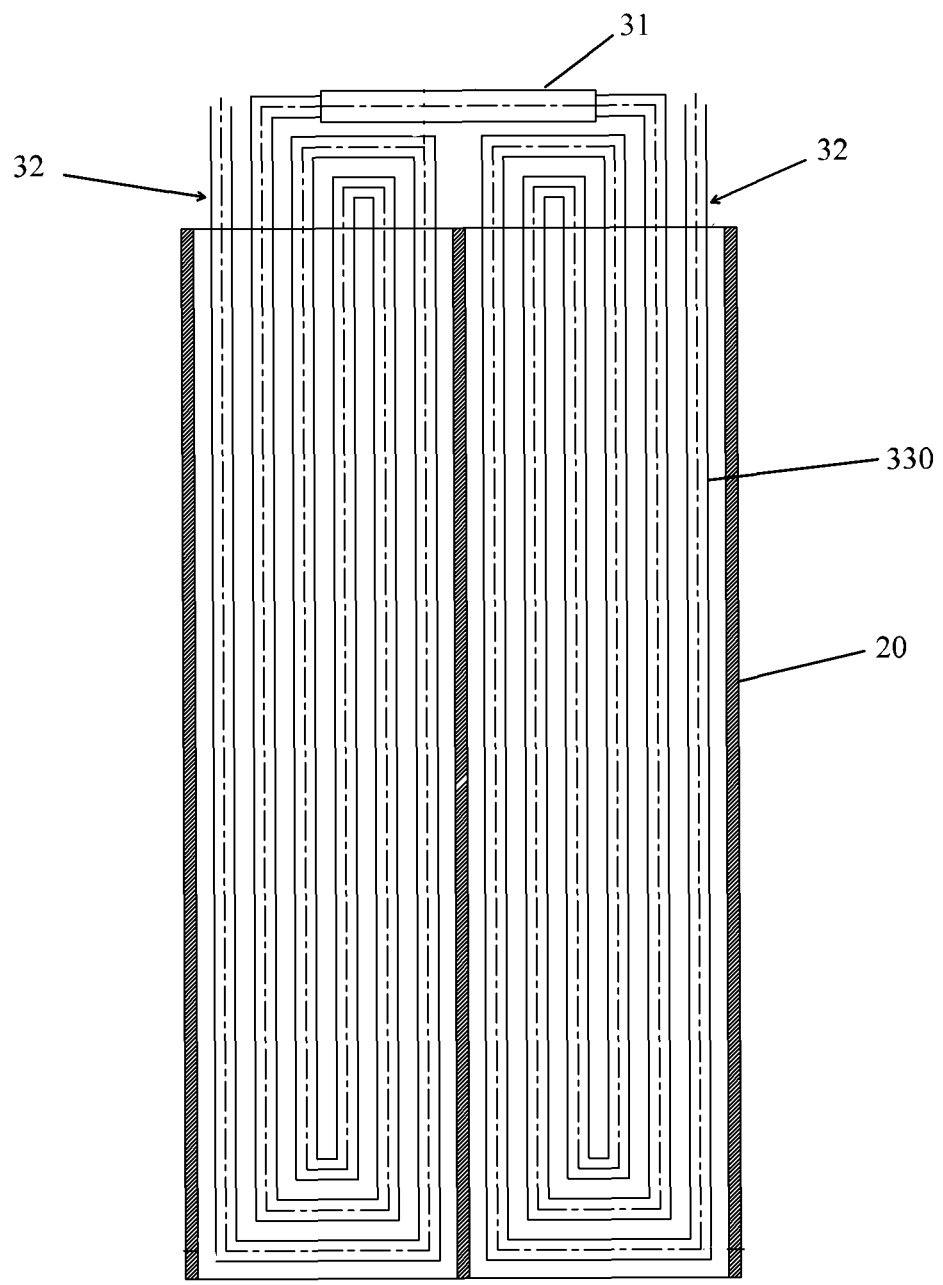
FIG. 7 is a side cross-sectional view of a portion of the holder of FIG. 1 showing heat transfer members received in pockets on an exterior surface of the holder.

Holder 15 may be configured to protect and maintain the shape of the flexible container. As depicted in FIGS. 1-3, the flexible container may conform to the geometry of the holder. Holder 15 also includes one or more external pockets 20 for receiving one or more heat transfer members 30. As best depicted in FIGS. 3 and 7, heat transfer fluid may be circulated through the heat transfer members (e.g., via a pump) and thereby through each pocket to cause freezing or thawing of biopharmaceutical materials held in a container held in the holder. Water or another fluid may be provided in pockets 20 (i.e., around the heat transfer members) to facilitate heat transfer between the heat transfer members and an exterior surface 22 of the holder. Pockets 20 may be formed by the connection of pocket structural members 25 to, or the monolithic formation relative to, exterior surface 22 of holder 15. A cavity 122 of each pocket may be bounded by exterior surface 22 and an interior surface 125 of each of structural members 25 as depicted in FIG. 4.

Holder 15 may be formed of a plastic material, and could also be made of a metal such as stainless steel or aluminum. For low temperature applications, polyethylene is preferred. By using plastic it is possible to make use of fabrication techniques such as rotational molding, blow molding, and thermoforming which enable significant cost and weight reductions as well as greater design flexibility.

Holder 15 may be formed monolithically (e.g., having 5 monolithic sides and an open top) or it may be formed in two or more portions which are connectable to each other, such as a clamshell design. Such separate portions may be mirror images of each other and the portions may allow nesting of the individual portions, thereby increasing the packing density when empty. Pocket structural members 25 may also be formed monolithically relative to a unitary holder (e.g., holder 15), or such multi-piece holders may be formed as mirror images of each other.

Holder 15 has interior surfaces 40 bounding a cavity 50 receiving container 10 and conforming to the geometry of container 10. Interior surfaces 40 may include opposing contact surfaces 41 which contact container 10 on opposite sides of container 10, and which may extend from a top end 118 to a bottom end 119 of holder 15. Holder 15 has a top opening 23 to permit access to cavity 50 for the installation of container 10 prior to filling and for the removal thereof after draining Holder 15 may include features (e.g., openings, valves) to permit pass-through of ports for filling, draining, sampling, etc., of the biopharmaceutical materials. Holder 15 may optionally have features (e.g., grooves or cavities) to give additional allowance for seams of container 15 in order to avoid stressing them during shipping and handling. Holder 15 may also have features such as tubing clips or protective pockets to position, protect, and/or organize components external to the container such as tubing, clamps, connectors, valves, instruments, filters, etc.

As indicated, holder 15 includes one or more pockets 20 which may be on its longitudinal faces or could be on substantially all its outer surfaces. The pockets will preferably occupy as much surface area as possible to promote heat transfer between the heat transfer members held therein and biopharmaceutical materials held in container 10. Each pocket has an opening 26 at a top end thereof to allow each pocket to receive some portion of one of removable heat transfer members 30. Each pocket may extend from top end 118 to bottom end 119 of holder 15.

Also, pockets provide structural stiffness at the connection points of pocket structural members 25 to exterior surface 22 of holder 20 (i.e., where the two walls in the double-walled structure are brought together to form ribs at "kiss-off" points). The connection of pocket structural members 25 to exterior surface 22 resists hydrostatic pressure, external forces, and the expansion and contraction of the biopharmaceutical materials in container 10 during freezing and thawing. As depicted in FIG. 4, pocket structural members 25 may be formed monolithically as a single monolithic portion 28 such that recessed portions 27 connect to exterior surface 22 and pocket forming portions 29 extend away from exterior surface 22 to form pockets 20.

Also, the pockets receive the heat transfer members to provide minimal separation between the heating/cooling surface (i.e., the outer surfaces of the heat transfer members) and the biopharmaceutical materials inside holder 15 and container 10. Pocket structural members 25 may be connected to exterior surface 22 such that the pockets are liquid-tight (e.g. via sealing, sealed connections, or monolithic construction). This allows each pocket to hold water or another liquid to promote heat transfer between heat transfer members 30 in pockets 20 and holder 15 thereby promoting heat transfer relative to biopharmaceutical materials held in container 10.

More specifically, when heat transfer members 30 are inserted into the pockets, an annular gap exists between each heat transfer member and interior surface 125 of each of pocket structural members 25 and exterior surface 22. Such a gap may be desirable to facilitate introduction and removal of the heat transfer members into the pockets by allowing a clearance around each heat transfer member. However, any such gap would reduce the heat transfer between the heat transfer member and holder 15 and thus biopharmaceutical materials held in container 10. The introduction of a liquid (e.g., water) into the pockets (i.e., pockets 20) provides a thermal bridge from the heat transfer members to exterior surface 22 and thus container 10 and the biopharmaceutical materials held therein. Thus, any reduction in heat transfer is avoided or reduced by flooding the gap with a liquid, such as water. Liquid may be introduced into the pockets via a liquid distribution manifold 31 which may also allow the evacuation of such pockets therethrough as depicted in FIG. 3, for example.

After the freezing of a liquid held in pocket 20, it is further desirable that any spaces or gaps, which could provide an air insulative effect, be minimized between the frozen liquid and exterior surface 22. Any such gap would reduce the heat transfer between heat transfer member(s) 30 and the contents of container 15. Exterior surface 22, interior surfaces 125 of pocket structural members 25, and/or heat transfer members 30 may include projections or a textured surface to promote bonding between the liquid as it freezes and thereby inhibit the formation of any such insulative air gaps or spaces.

Figure 5:
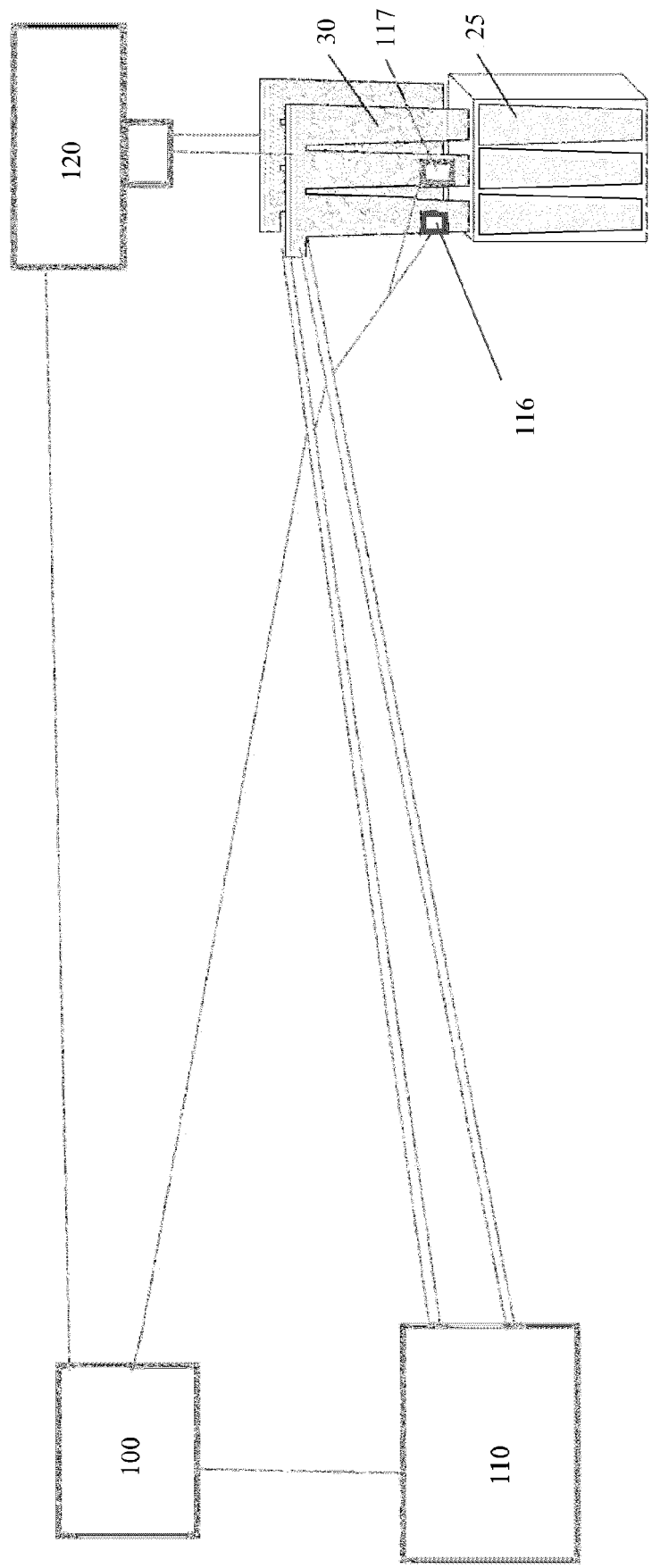
FIG. 5 is a block diagram showing the holder of FIG. 1 receiving heat transfer members coupled to a pump and controller, along with the heat transfer members being lowered from a hoist into pockets of the holder.

Also, heat transfer members 30 may be moved into pockets 20 when cooling or heating is desired for biopharmaceutical materials held in container 10, and may be removed when the biopharmaceutical materials held in the container have reached the desired temperature (e.g., a thawing or freezing temperature) as depicted in FIG. 2. Such insertion and removal may be done by a retracting device 120 (e.g., a powered hoist or a hand-driven mechanism as depicted in FIG. 5) for raising and lowering such heat transfer member(s), for example.

Figure 8:
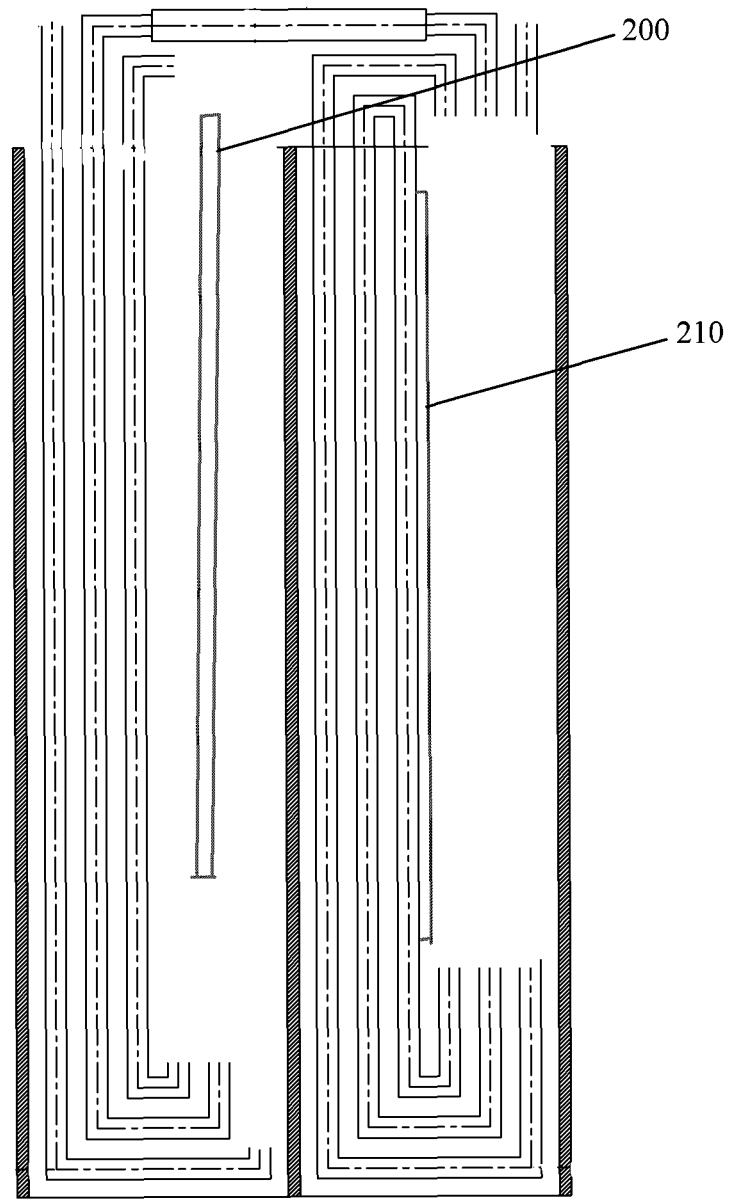
FIG. 8 is side cross-sectional view of the holder of FIG. 1 showing heat transfer members received in pockets thereof, along with supplemental heating members.

Heat transfer members 30 may include one or more conduits having heat transfer liquid flowing therethrough to control a temperature of holder 15, container 10 and biopharmaceutical materials held therein. A pump 110 (FIG. 5) may be coupled to a controller 100 (FIG. 5) such that the flow of heat transfer liquid flowing through heat transfer members 30 may regulate a temperature of biopharmaceutical materials held in container 10 in holder 15. Heat transfer members 30 (e.g., conduits used to flow heat transfer fluid) could include a supplemental heater (e.g., one or more electrical resistive coils 210 as depicted in FIG. 8) on an outside surface thereof to keep open a pathway (i.e. an unfrozen path) during freezing of biopharmaceutical materials in container 10 to allow movement of liquid in pockets 30. More specifically, such a heater may direct the expansion of ice in the annular gap (i.e., between heat transfer members and exterior surface 22 and interior surfaces 125) upward rather than allow it to deform exterior surface 22 or pocket structural member 25. For example, the supplemental heater may be turned on for an interval at the start of a freeze operation to keep the liquid channel clear of ice, thereby providing an exit path for the annular liquid that would otherwise become trapped and pressurized once frozen. Alternatively, a separate probe (e.g., a probe 200 as depicted in FIG. 8) containing a heating element may be utilized instead of a heating element on the surface of the heat transfer members. Such a separate probe may be sized to maintain a liquid channel open between the center of the pocket and the top surface of the ice. In another unillustrated example, such a supplemental heater or probe may be utilized in an interior of a container (e.g., container 10) holding biopharmaceutical materials therein such that an exit path is maintained for annular liquid biopharmaceutical materials that may otherwise become trapped and pressurized once the biopharmaceutical materials are frozen.

Heat transfer members 30 may have a finger-like structure including an upper common segment or rail 31 and one or more digits of fingers 32 extending downwardly and having a shape to conform to pockets 20 as depicted in FIG. 3. The fingers may be tapered from the rail toward the pockets to make insertion and removal easier. Also, the heat exchangers may be configured to promote heat transfer on the container-facing side of each finger and suppress heat transfer on the opposite side, e.g., via insulation on the opposite side.

As described above, heat transfer members 30 may be cooled and heated by circulating a heat transfer fluid through internal passages thereof. For example, silicone oil, such as Dow Syltherm HF, may be used as a heat transfer fluid over the temperature range of approximately −70° C. to +40° C. The temperature and flow rate of the heat transfer fluid may be controlled by an external device, such as a recirculating chiller such as Sartorius Stedim Biotech CU5000 Thermal Control Unit. In one example depicted in FIG. 7, fingers 32 include a coiled conduit 33 received in one or more of pockets 20 as depicted in the cross-sectional view depicted in this figure. As described above, rail 31 may connect various fingers extending therefrom. The fingers may be formed of stainless steel, for example. Also, such conduits (e.g., heat transfer member 30) may be directly inserted into pockets 20 or may be encased in a protective casing with such casing being inserted into pockets 20.

Alternatively, instead of flowing liquid through heat transfer members, the heat transfer members may be cooled by evaporation and flow of a cryogen such as liquid nitrogen, liquid argon, or liquid carbon dioxide through the internal passages thereof. Further, the heat transfer members could be cooled by evaporation and flow of a refrigerant such as R-507 through internal passages. Also, the heat transfer members could be heated by electrical resistance heaters.

The heat transfer members may optionally be cooled and heated by elements providing for high thermal conductivity between the fingers and an active cooling/heating area. Examples of high thermal conductivity elements include heat pipes and anisotropic graphite sheet.

Pockets 30 of holder 15 may be tapered from the opening to ease insertion and removal of heat transfer members 30. Also, as described above holder 15 may be engageable with, or connected to, base 17 having a plurality of recesses or grooves 117 for receiving and supporting bottom end 119 of holder 15. Base 17 may be configured (e.g., shaped and dimensioned) to permit transport of the holder 15 having container 10 therein by conventional pallet handling equipment such as a pallet jack and forklift.

In one example, holder 15 (e.g. exterior surfaces 22 thereof) may be concave towards the interior thereof (i.e., cavity 50) prior to freezing of biopharmaceutical materials held in container 10 in holder 15 such that when a hydrostatic pressure loads the walls of holder 15 (i.e., due to the freezing), the walls flex outwardly to form a shape that is approximately a rectangular prism. The degree of concavity may be varied across the height of the box to account for variations in deflection due to such freezing.

Figure 6:
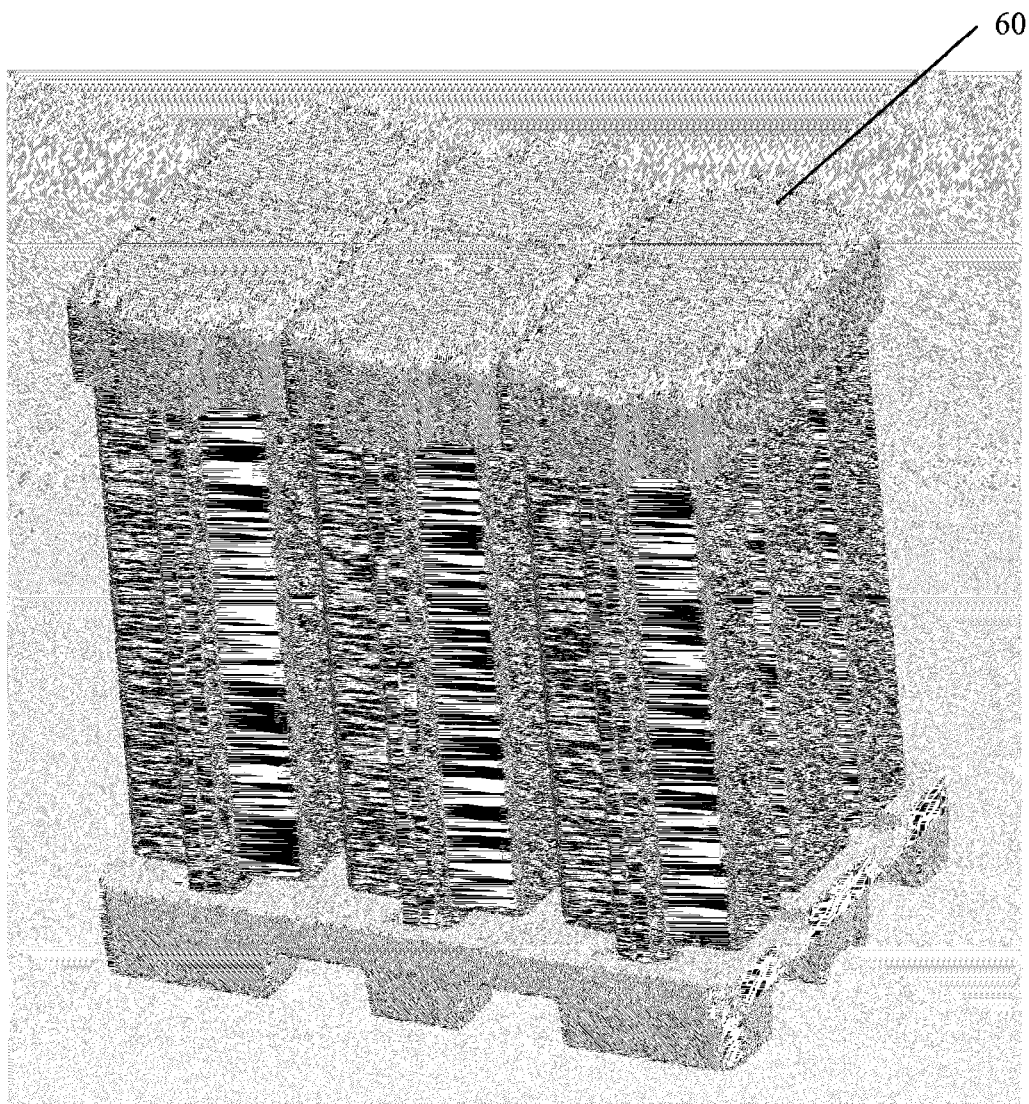
FIG. 6 is a perspective view of three holders as shown in FIG. 1 depicted together on a pallet base and having covers thereon.

Holder 15 may have a cover 60 to provide complete enclosure of the container/box assembly as depicted in FIG. 6. The cover may be integral or separate. Holder 15 and/or pockets 30 connected thereto may optionally have insulation on exterior surfaces to minimize temperature variations during transport. The insulation may be removable or fixed. The insulation may optionally be embedded in a double-wall structure.

Although container 10 may have any useful geometry, in one embodiment the container is a rectangular prism having gusseted construction, such as Sartorius Stedim Biotech Flexel 3D. The width of the container, in the axis normal to the plane of heat transfer members 30, is specified to produce a desired heating and cooling response. For example, the width may be much smaller than the depth or height so as to minimize the time required to freeze or thaw the contents of the container. However, the depth and height are typically constrained to a practical maximum of approximately one (1) meter by storage and shipping/handling considerations. In one example, the container (e.g. container 10) could be 23.25 inches by 7.87 inches by 42 inches. Such a container would have a usable volume of about 110 liters and a 15% margin for expansion and safety.

Container 10 may be formed of a laminated film which includes a plurality of layers. Also a biocompatible product-contacting layer of the interior of flexible container 10 may be formed of a low density polyethylene, very low density polyethylene, ethylene vinyl acetate copolymer, polyester, polyamide, polyvinylchloride, polypropylene, polyfluoroethylene, polyvinylidenefluoride, polyurethane or fluoroethylenepropylene, for example. A gas and water vapor barrier layer may also be formed of an ethylene/vinyl alcohol copolymer mixture within a polyamide or an ethylene vinyl acetate copolymer. Further, flexible container 10 may include a layer with high mechanical strength (e.g. a polyamide), and an external layer with insulating effect to heat welding, for example, polyester. The layers may be compatible with warm and cold conditions and may be able to withstand ionizing and gamma irradiation for sterilization purposes.

Container 10 may be adapted to receive and contain frozen and/or liquid biopharmaceutical materials. In an embodiment, the biopharmaceutical materials may comprise protein solutions, protein formulations, amino acid solutions, amino acid formulations, peptide solutions, peptide formulations, DNA solutions, DNA formulations, RNA solutions, RNA formulations, nucleic acid solutions, nucleic acid formulations, antibodies and their fragments, enzymes and their fragments, vaccines, viruses and their fragments, biological cell suspensions, biological cell fragment suspensions (including cell organelles, nuclei, inclusion bodies, membrane proteins, and/or membranes), tissue fragments suspensions, cell aggregates suspensions, biological tissues in solution, organs in solution, embryos in solution, cell growth media, serum, biologicals, blood products, preservation solutions, fermentation broths, and cell culture fluids with and without cells, mixtures of the above and biocatalysts and their fragments.

As described above, container 10 may be configured (e.g., shaped and dimensioned) to be received in holder 15, which acts as a protector, supporting structure or frame for supporting flexible container 10, as depicted in FIGS. 1-5. Holder 15 may be configured to protect a container held therein during filling, transport, storage, and/or freezing of biopharmaceutical materials. For example, holder 15 may hold and protect container 10 during freezing of biopharmaceutical materials by heat transfer members 30.

Further, container 10 and/or holder 15 may optionally be equipped with one or more temperature sensors (not shown) to monitor the progress of a freeze/thaw of the biopharmaceutical materials in container 10 to detect temperature variations. The sensors may be single use, possibly installed prior to sterilization, or they may be reusable. Such sensor(s) may be located on the container wall (i.e., interior surfaces 40) and may be coupled to a controller, for example. Also, container 10 and/or holder 15 may optionally be equipped with one or more heat flux sensors (not shown) to quantify the rate of thermal energy ingress or egress from the container.

In another example, one or more temperature sensors may be located in one or more pockets 20 to measure the temperature of the liquid inside the pockets. Such sensors may be coupled to a control and utilized to determine when the heat exchangers can be removed (e.g., via a hoist) from the pocket(s) following freezing. This sensor may be mounted on the heat exchanger(s) to minimize instrumentation on holder 15. Further one or more sensor(s) (e.g., a sensor 116) may be utilized to determine whether the heat exchangers (e.g., heat transfer members 30) are fully seated in the pocket(s). Such sensor(s) will ideally be mounted on the heat exchanger to minimize instrumentation on holder 15.

In a further example, a sensor may determine whether the annular space in pocket 20 between the heat exchanger and exterior surface 22 of holder 15 and/or interior surface 125 of each of structural members 25 is fully flooded (e.g., by water or another liquid). Such a sensor (e.g., a sensor 117 in FIG. 5) may be mounted on the heat exchanger (e.g., one or more heat transfer members 30) to minimize instrumentation on holder 15. If such a sensor is a pressure sensor, as is commonly used to measure liquid level by correlating with hydrostatic pressure, then the sensor may be located in piping used to move the liquid (e.g., water) in and out of the pockets (e.g. via manifold 31). Also, holder 15 may optionally have a location for a data logger to be affixed.

Also, it will be understood by one skilled in the art that various holders (e.g., holder 15) may have cavities (e.g., cavity 50) configured (e.g., shaped and dimensioned) to receive various sized containers (e.g., container 10). Although the containers are described herein as flexible containers, the containers may be made of a semi-rigid material such as polyethylene or the like. An example of such a container could include a container similar to a standard plastic milk jug. Containers made of such similar semi-rigid materials may benefit from additional rigidity supplied by attachment (e.g., fixedly or releasably) to a holder, for example. Further, the containers whether formed of a rigid, flexible or semi-rigid material, contain outer surfaces which may contact the interior surfaces of a holder (e.g., holder 15) which may be formed of a material to facilitate heat transfer to and from a container (e.g., container 10) held in such a holder (e.g., holder 15) coupled to a temperature control device (e.g., heat transfer members 30). Also, such containers could be of various shapes including a tapered shape (e.g., toward a closed end of a holder receiving the container) to improve the efficiency of a freezing/thawing cinetic and orientate ice expansion toward a top of the container. Further, such containers could be a two-dimensional shaped flexible container (i.e., two films attached to one another) or a three dimensional tapered container, for example.

Figure 9:
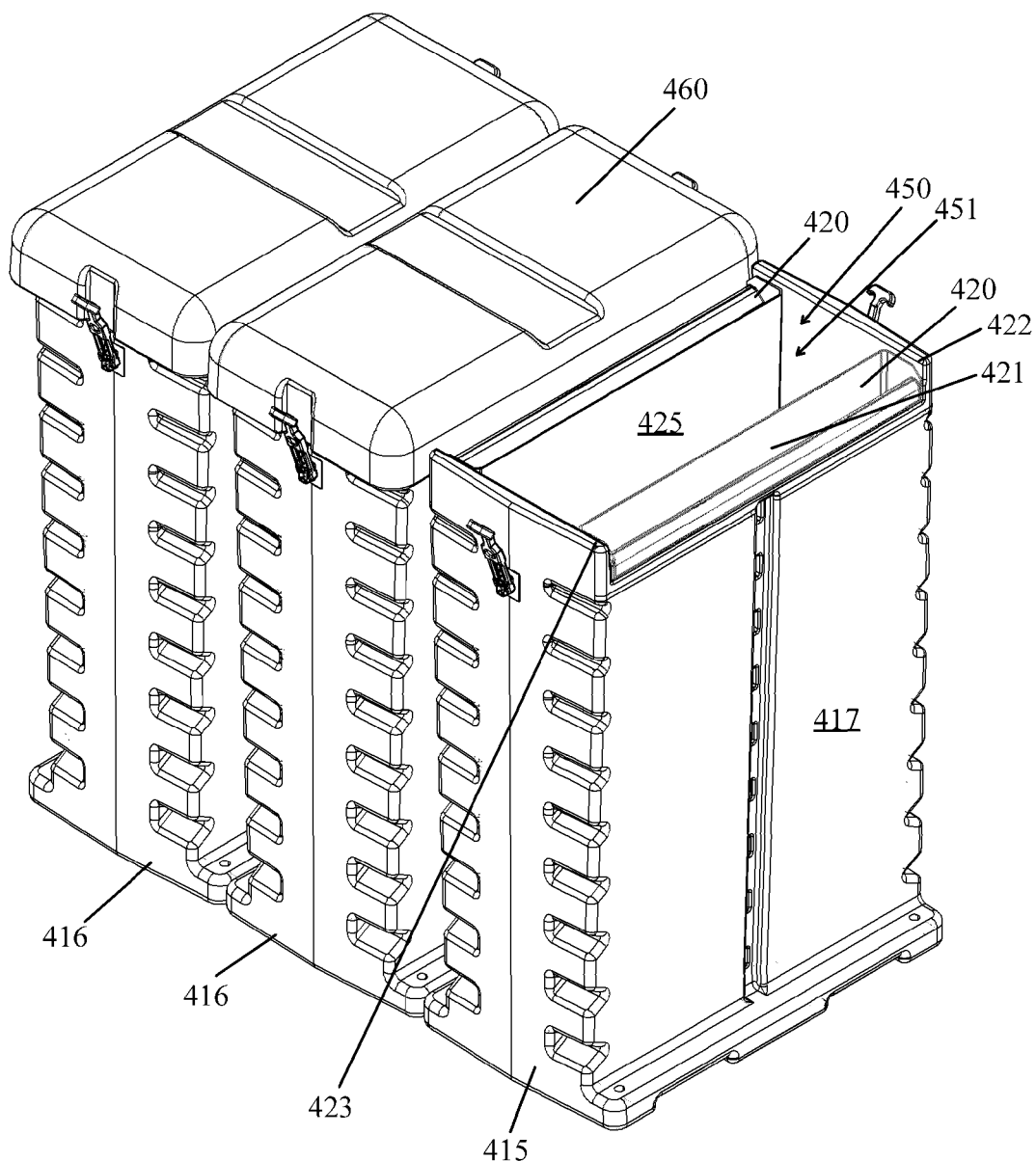
FIG. 9 is a perspective view of a plurality of holders, one of which has a top portion removed showing a cavity receiving two pockets therein, in accordance with another embodiment of the present invention.
Figure 10:
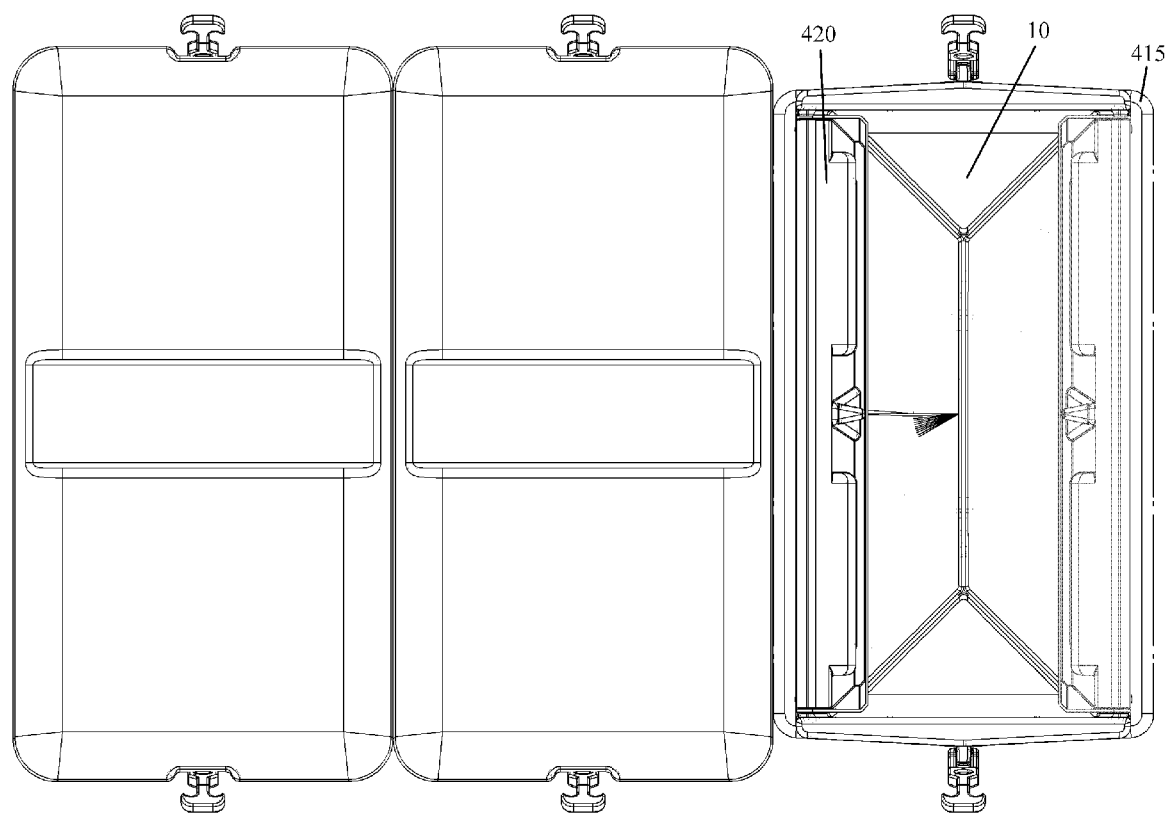
FIG. 10 is a top elevational view of the plurality of holders of FIG. 9 showing a container received in a holder having a top portion removed.
Figure 11:
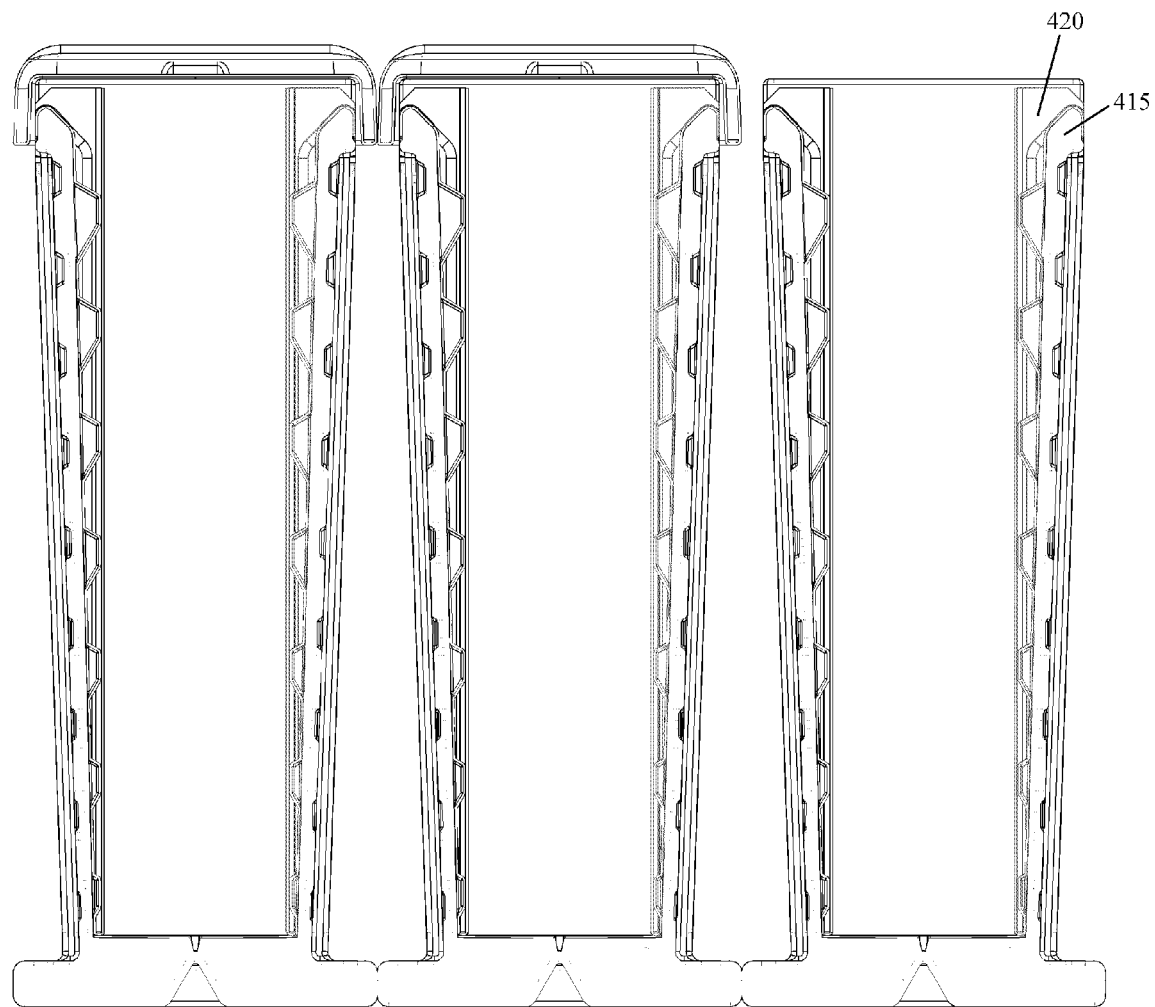
FIG. 11 is a side elevational view of the plurality of holders of FIG. 9.

In another embodiment depicted in FIGS. 9-11, a holder 415 may be connected to one or more other holders 416, all of which being configured (i.e. shaped and dimensioned) to receive a flexible container for receiving biopharmaceutical materials, such as flexible container 10 described above. In particular, holder 415 may receive two pockets (or sleeves) 420 in a holder cavity 450 along opposite longitudinal sides thereof, which may be separate from, or connected to, holder 415. Container 10 may be received between pockets 420 in a central portion 451 of cavity 450. Also, container 10 could be shaped to correspond to walls 417 of holder 415.

Each of pockets 420 may be configured (i.e. shaped and dimensioned) to receive one or more heat transfer members, such as heat transfer members 30 described above, in a cavity 421 thereof. As depicted FIGS. 9-11, cavity 421 may be open from a first end 422 to an opposite end 423 of holder 415. In another example, cavity 421 could include separated portions, such as pockets 20 described above. One or more heat transfer members may be received in cavity 421. Pockets 420 may have walls 425 which are more flexible and/or thinner than walls 417 of holder 415. Further, walls 417 may be more insulative than walls 425 thereby inhibiting heat transfer from holder 415. Holder 415 and pockets 420 may be formed of a plastic material or stainless steel, for example. Holder 415 and pockets 420 could be formed by rotomolding.

As described above relative to holders 15 and pockets 20, pockets 420 may receive heat transfer members 30 to control a temperature of container 10 received in cavity 450. Pockets 420 may be configured to hold a liquid, such as water, to hold a solid/liquid mixture and/or to hold a solid, such as ice. Liquid may be inserted into, and removed from, cavity 421 of each of pockets 420 using dip tubes in contrast to distribution manifold 31 described above relative to pockets 20. The temperature of biopharmaceutical materials held in container 10 may be controlled while container 10 is received in cavity 450 contacting pockets 420 by controlling a temperature of heat transfer members 30 received in pockets 420 similar to the description above relative to heat transfer members 30 received in pockets 20.

As depicted in FIGS. 9-11, holder 415 is missing a cover but each of holders 416 include such a cover 460. Holder 415 may also receive such a cover which is configured to seal and protect container 10 received in cavity 450 and is configured to allow transport of holder 415 holding container 10 having biopharmaceutical materials therein.

Figures 12, 13, 14:
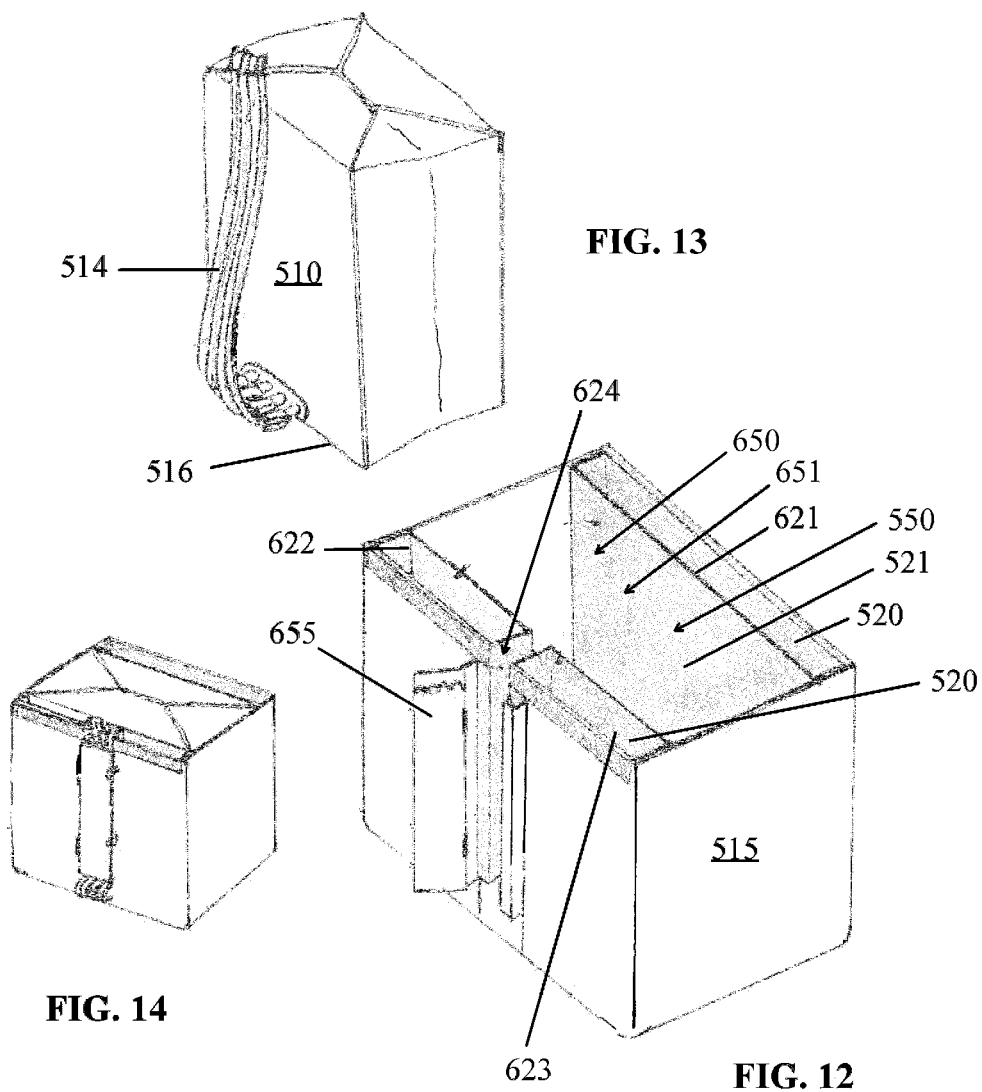
FIG. 12 is a perspective view of a holder in accordance with a different embodiment of the present invention.
FIG. 13 is a perspective view of a container configured to be received in the holder of FIGS. 12.
FIG. 14 is a perspective view of a further embodiment of a container in accordance with the present invention.

Another example is depicted in FIGS. 12-14, which is a variant of holder 415 described above. In particular, a holder 515 may be configured (i.e. shaped and dimensioned) to receive a flexible container for receiving biopharmaceutical materials, such as a flexible container 510 depicted in FIG. 13. Container 510 may include filling and draining conduits 514 connected near a lower end 516 of container 510.

Holder 515 may receive three pockets (or sleeves) 520 in a holder cavity 550 along opposite longitudinal sides thereof, which may be separate from, or connected to, holder 515. More specifically, a first pocket 621 may be located opposite a second pocket 622 and a third pocket 623. Second pocket 622 and third pocket 623 may be separated by a conduit passageway 624. Conduits 514 may be received in conduit passageway 624 when container 510 is received in a central portion 651 of a cavity 650 of holder 515. Holder 515 may also include a door 655 which allows access to conduits 515 held in conduit passageway 624.

In a further unillustrated example, a holder similar to holder 515 may include a conduit passageway without a door allowing access thereto from an outside of the holder. Instead, conduits of such a container may be inserted into a conduit passageway from an opening on a topside thereof. For example, such a conduit passageway could be a groove or channel in a side wall of such a holder. In yet a further example, a holder similar to holder 515 may include an exit opening to allow the conduits to pass therethrough. Such conduits may be connected to an exterior of the holder via any manner of connection to inhibit damage to such conduits.

A typical process for processing and/or preserving a biopharmaceutical material is described as follows. One or more containers (e.g., container 10) is received in a holder (e.g., holder 15, holder 415, holder 515) as depicted in the figures. Liquid biopharmaceutical material, may be inserted through a conduit into container 10. A heat exchanger (e.g., heat transfer member(s) 30) is inserted into pockets (e.g., pockets 20, pockets 420, pocket 621, pocket 622, pocket 623) and the pockets may be flooded with water. The heat exchanger is cooled (e.g., by flowing heat transfer fluid therethrough) until the contents of the container are frozen or the contents are at a desired temperature for transport and storage. The liquid in the pocket surrounding the heat transfer member may freeze first and create an ice bridge between the heat exchanger and a pocket wall (e.g., exterior 22 and interior 125). At the conclusion of the freeze process, the heat exchanger may be briefly warmed (e.g., via heat transfer member 30, or supplemental heater 210) until the ice in the annular gap is melted. The heat exchanger is removed from the pockets by a hoist or other raising mechanism. The liquid is removed from the pockets via a manifold or dip tubes, for example. Holder 15 may then be removed from a station housing the heat exchanger.

In one example, it may be desirable to mix the contents of container 10, either during or following a thaw of biopharmaceutical materials in container 10. Mixing may increase the rate of thawing and improve homogeneity. Such mixing may be performed by various methods. In one example, container 10 held in a holder (e.g., holder 15, holder 415, holder 515) may be agitated, i.e., moved to induce movement inside the container. The movement may be random, periodic, etc. A path for such movement could be linear, orbital, etc. In another example, recirculation may be performed. Specifically, liquid may be pumped from the container at one point and introduced at another, optionally through a distribution manifold. In a further example, a vibromix may be done. In particular, a probe having a plate with one or more angled orifices connected normally to a shaft is driven along the long axis of the shaft with a periodic linear stroke. The angled orifices in the plate develop a one-way flow in the liquid. The probe may be frozen in place and then heated at the start of the thaw to develop a clear working volume free of ice. The probe is ideally single-use to avoid the complication of inserting a reusable probe into a sterilized container. In a final example, an impeller may be frozen in place and then heated at the start of the thaw to develop a clear working volume free of ice. The impeller is ideally single-use to avoid the complication of inserting a reusable probe into a sterilized container.

Also, a holder (holder 15, holder 415, holder 515) and the contents of container 10 may be monitored throughout the processing described above via the monitoring devices described above and/or a temperature sensor, pH sensor or sensor for monitoring any characteristic of the biopharmaceutical materials held therein. Data corresponding to such monitoring may be stored on a storage medium (e.g., a computer disk, processor, flash drive, etc.) of a controller or computing unit, which may later be transferred to a computing unit for analysis. Alternatively, the monitoring device may be coupled to a computing unit during the processing steps, (e.g., via a computer cable or wirelessly). Further, the thawing steps described above may be accomplished via various mixing mechanisms as described above.

From the above description, it will be understood to one skilled in the art that the containers described herein may be adapted for use in holders of various shapes or sizes. Further, the holders may be adapted to receive containers of various shapes or sizes. These holders or support structures may be configured for long or short term storage of the containers containing biopharmaceutical materials in liquid or frozen state, or may be adapted to transport the flexible containers containing biopharmaceutical materials in liquid or frozen state. Further, these holders and containers may be adapted for utilization with materials other than biopharmaceutical materials.

While the invention has been depicted and described in detail herein, it will be apparent to those skilled in the relevant art that various modifications, additions, substitutions and the like can be made without departing from the spirit of the invention and these are therefore considered to be within the scope of the invention as defined in the following claims.

The invention claimed is:

1. A system for use in freezing, thawing, transporting, or storing biopharmaceutical materials, said system comprising:
    a container means for holding biopharmaceutical materials therein;
    a holder having a holder cavity for receiving said container means, said holder comprising a plurality of pockets having interior surfaces bounding said holder cavity;
    said plurality of pockets located on opposite sides of said holder cavity and contacting an outer surface of said container means, each pocket of said plurality of pockets comprising a pocket cavity;
    a heat transfer member for actively controlling a temperature of biopharmaceutical materials held in said container means, said heat transfer member received in a first pocket cavity of at least one pocket of the plurality of pockets.

2. The system of claim 1 further comprising a mechanism configured to insert and remove said heat transfer member relative to said pocket cavity.

3. The system of claim 1 wherein said pocket comprises an opening on a top end thereof for receiving said heat transfer member.

4. The system of claim 1 wherein said pocket is configured to hold a liquid therein, the liquid promoting heat transfer between said heat transfer member received in said pocket cavity and said holder to control the temperature of the biopharmaceutical materials held in said container.

5. The system of claim 1 further comprising a location sensor for determining when said heat transfer member is properly positioned in said pocket cavity.

6. The system of claim 1 further comprising a sensor for determining when said cavity is adequately filled with liquid.

7. The system of claim 1 further comprising a supplemental heater separate from said heat transfer member to warm the liquid in said pocket cavity to maintain a pathway clear of ice during a freezing operation to form an exit path for a portion of the liquid.

8. The system of claim 1 further comprising a supplemental heater received in said container means to maintain a pathway clear of frozen biopharmaceutical materials in said container means.

9. A system for use in freezing, thawing, transporting, or storing biopharmaceutical materials, said system comprising:
    a container means for holding biopharmaceutical materials therein;
    a holder having a plurality of pockets contacting an outer surface of said container means, each pocket of said plurality of pockets comprising a pocket cavity;
    said holder having a bolder cavity for receiving said container means, said plurality of pockets located on opposite sides of said holder cavity and comprising an interior surface bounding said holder cavity, said interior surface comprising two contact surfaces contacting opposite sides of said container means.

10. The system of claim 9 wherein each pocket of said plurality of pockets comprises an opening on a top end thereof for receiving a heat transfer member for controlling a temperature of biopharmaceutical materials held in said container.

11. The system of claim 10 wherein each pocket of said plurality of pockets is configured to hold a liquid therein, the liquid promoting heat transfer between said heat transfer member received in said pocket cavity and a wall of each pocket to control the temperature of the biopharmaceutical materials held in the container means when said heat transfer member is received in said cavity.

12. The system of claim 9 wherein each pocket of said plurality of pockets is tapered from said opening to ease insertion and removal of said heat transfer member.

13. A method for use in freezing, thawing or storing biopharmaceutical materials, the method comprising:
    receiving a container means holding biopharmaceutical materials in a holder cavity of a holder;
    a plurality of pockets of the holder contacting an outer surface of said container means, each pocket of the plurality of pockets comprising a pocket cavity, the plurality of pockets located on opposite sides of the holder cavity;
    receiving a heat transfer member in at least one pocket cavity of the plurality of pockets; and
    actively controlling a temperature of the heat transfer member to control a temperature of the biopharmaceutical materials held in the container means.

14. The method of claim 13 further comprising inserting a liquid into the pocket cavity and wherein the controlling the temperature comprises controlling the temperature of the heat transfer member to freeze the biopharmaceutical materials, and the controlling the temperature causes a freezing of the liquid to promote heat transfer between the heat transfer member and a wall of the pocket.

15. The method of claim 13 further comprising introducing a supplemental heater into the pocket to provide a pathway clear of ice during a freezing operation caused by the controlling the temperature of the heat transfer member.

16. The method of claim 13 further comprising introducing a supplemental heater into the container means to provide a pathway clear of frozen biopharmaceutical materials during a freezing operation caused by the controlling the temperature of the heat transfer member.

17. The method of claim 13 further comprising inserting a liquid into the pocket cavity and wherein the controlling the temperature comprises controlling the temperature of the liquid to promote heat transfer between the heat transfer member and a wall of the pocket to control a temperature of the biopharmaceutical materials.

18. The method of claim 13 wherein the actively controlling the temperature of a heat transfer member comprises actively controlling the temperature of the heat transfer member to freeze the biopharmaceutical materials in the container means.

* * * * *